(12) United States Patent
Bernardo et al.

(10) Patent No.: US 7,469,596 B1
(45) Date of Patent: Dec. 30, 2008

(54) MEASUREMENT OF CONSTITUTIVE PROPERTIES OF A POWDER SPECIMEN SUBJECT TO COMPRESSIVE AXIAL AND RADIAL LOADING, USING EDDY CURRENT SENSING

(75) Inventors: Alexander Beltran Bernardo, San Antonio, TX (US); Gary Lane Burkhardt, Adkins, TX (US); Arthur Edwin Nicholls, Helotes, TX (US); Walter Mac Gray, San Antonio, TX (US)

(73) Assignee: Southwest Research Institute, San Antonion, TX (US)

( * ) Notice: Subject to any disclaimer, the term of this patent is extended or adjusted under 35 U.S.C. 154(b) by 0 days.

(21) Appl. No.: 11/872,345

(22) Filed: Oct. 15, 2007

(51) Int. Cl.
*G01N 3/08* (2006.01)
*G01B 5/30* (2006.01)

(52) U.S. Cl. .......................................... 73/818; 73/760

(58) Field of Classification Search ................... 73/760, 73/818
See application file for complete search history.

(56) References Cited

U.S. PATENT DOCUMENTS

| | | | | |
|---|---|---|---|---|
| 3,664,473 | A * | 5/1972 | Hendershot et al | 192/21.5 |
| 4,852,451 | A * | 8/1989 | Rogers | 86/33 |
| 5,864,239 | A * | 1/1999 | Adams et al. | 324/636 |
| 7,288,941 | B2 * | 10/2007 | Redko et al. | 324/450 |

* cited by examiner

*Primary Examiner*—Max Noori
(74) *Attorney, Agent, or Firm*—Baker Botts L.L.P.

(57) ABSTRACT

A method and system for measuring constitutive properties, such as radial strain, on a specimen of power or other granular material while the specimen is subject to compressive axial and radial loading. The specimen fills a pliable sleeve that has a conductive band around its circumference. An eddy current coil is placed around the sleeve, and used to provide a response signal that indicates the diameter of the sleeve, which in turn indicates radial strain.

13 Claims, 2 Drawing Sheets

MEASUREMENT OF CONSTITUTIVE PROPERTIES OF A POWDER SPECIMEN SUBJECT TO COMPRESSIVE AXIAL AND RADIAL LOADING, USING EDDY CURRENT SENSING

TECHNICAL FIELD OF THE INVENTION

This invention relates to measuring constitutive properties, such as radial strain, on a specimen of powder or other granular material while the specimen is subject to compressive axial and radial loading.

BACKGROUND OF THE INVENTION

The relationship between stress and strain of powders or granular materials can be difficult to determine. Unlike a specimen of solid material, a specimen of powder cannot be easily placed under uniaxial stress and examined. For example, for testing steel, a small piece of steel can be used as a specimen, placed under uniaxial stress, whereupon the resulting strain can be measured.

Because of their inherent nature, powders and granular materials must first be loaded in all three directions (triaxially) in an initial hydrostatic (pressure all around) condition. This permits the load on one of the axes to be increased to obtain the strain response of the loaded axis.

One approach to loading a specimen of powder triaxially is to provide a specimen having a right circular cylinder geometry. The specimen is subjected to constant confining pressure, using hydraulic pressure in the radial direction while varying the load in the long axis with mechanical means. This allows measurement of strain in the long axis, but measurement of strain in the radial direction becomes challenging, as strains in that direction can be upwards of 50%. A common strain gage is inadequate for this type of measurement.

For powders, properties such as the relationship between stress and strain or the Poisson's ratio, are referred to as "constitutive" properties. Once known, these properties can be used to predict the behavior of powders for diverse applications.

To determine constitutive properties, a small specimen of powder (or other granular material) can be evaluated, and its measured properties can then be used to predict the behavior of large amounts of the powder. The measurements can be used in simulations and other calculations. For example, if the properties of a sand specimen were to be measured, the penetration of a ballistic projectile into sandy terrain could then be simulated. If, in another example, measurements were made on an asteroid's response to a human-induced impact event, the results could be compared with simulations of the event using material characteristics of a catalog of powders and granular materials to verify the asteroid's composition.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The following description is directed to a method and system for measuring radial strain of powders and granular materials subject to compressive axial loading while radial pressure is being applied with hydraulic fluid.

Figure 1:
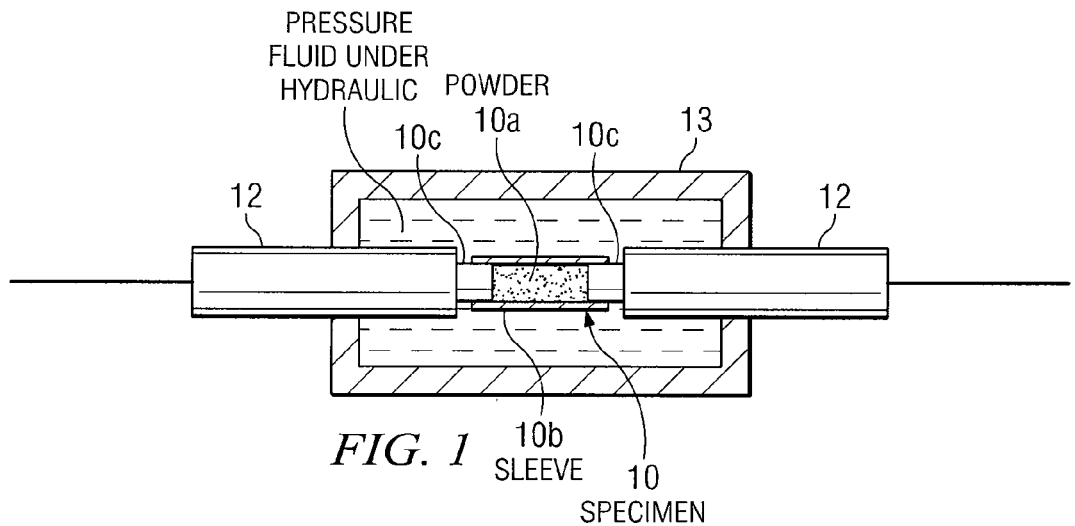
FIG. 1 illustrates a powder specimen that is compressed by both axial loading and hydraulic confinement.

FIG. 1 illustrates a specimen 10 subject to both axial and radial compression. The specimen 10 is a sample of a powder of interest 10a, contained by a cylindrically shaped pliable sleeve 10b and two plug-type end caps 10c.

FIG. 1 further represents equipment for loading the specimen 10, shown representatively by two opposing loading bars 12 and a hydraulic chamber 13, which are part of larger loading equipment. Examples of suitable equipment for applying axial loading are an MTS servo-hydraulic machine, or a Split-Hopkinson Pressure Bar technique. The loading bars 12 are moveable into chamber 13, which is filled with a hydraulic fluid for the purpose of applying a constraining radial force on the specimen 10.

Sleeve 10b may be made from various materials, but requires rigidity at small stresses and flexibility at high stresses. An example of a suitable material for sleeve 10b is Teflon or some other elastomeric material. The material and thickness of sleeve 10b can be adjusted to provide the desired amount of axial and radial compression for the particular powder 10a under test.

End caps 10c are made from a material that can withstand the axial loads described below. Examples of suitable materials are steel and ceramic.

For purposes of this description, a "powder" is used in a general sense to apply to any type of powder or granular material that is processed by applying compressive loading. An example of a suitable specimen size is 0.25 inches diameter and 0.5 inches long. Other specimen geometries and sizes may be used.

As explained further below, sleeve 10b is made from, contains, is coated with, or is encircled by, a conductive material.

In practice, one cap 10c is first inserted into one end of sleeve 10b, which is then filled with powder or other granular material of interest from the other end. The powder is compacted into the sleeve 10b, and the other cap 10c is inserted in the open end of the sleeve 10b. As a result, the powder is symmetrically sandwiched between the caps 10c.

The end caps are each axially slideable into their respective end of sleeve 10b. In the example of FIG. 1, each end cap 10c extends beyond sleeve 10b so that it can be pressed into sleeve 10b thereby compressing the powder 10a.

The specimen 10 is positioned between the loading bars 12 in the chamber 13. The chamber 13 is then filled with the hydraulic fluid. The hydraulic fluid and the loading bars are simultaneously loaded to generate hydrostatic pressure on the specimen 10. That is, the axial load and the radial load impart equal pressure on the specimen 10 in all directions. The axial load from the loading bars 12 is translated to the powder 10a through the caps 10c. As stated above, the caps 10c are slideable within sleeve 10b so that the powder is compressed and exerts a radial response against the sleeve 10b. This causes sleeve 10b to increase in diameter.

Once hydrostatic pressure is achieved, the axial loading is increased and the axial and radial strain response can be measured. The axial load can be slow or fast (ranging from 10e-5 strain per second to 10e3 strain per second). The hydraulic fluid continues to impart confining pressure on specimen 10, while it is subject to the axial loading. The hydraulic loading is kept at a constant pressure while the axial load is increased.

In practice, the equipment is often operated so that the initial loading is uniform on the ends (from the axial loading) and sides (from the radial loading) of the sleeve 10b. The measurement of strain in the axial direction is achieved using methods not discussed here.

Under the loading conditions of FIG. 1, the specimen 10a can be made to undergo large radial strains (up to 50%). Strain gages are not useful for measuring this type of strain.

Figure 2:
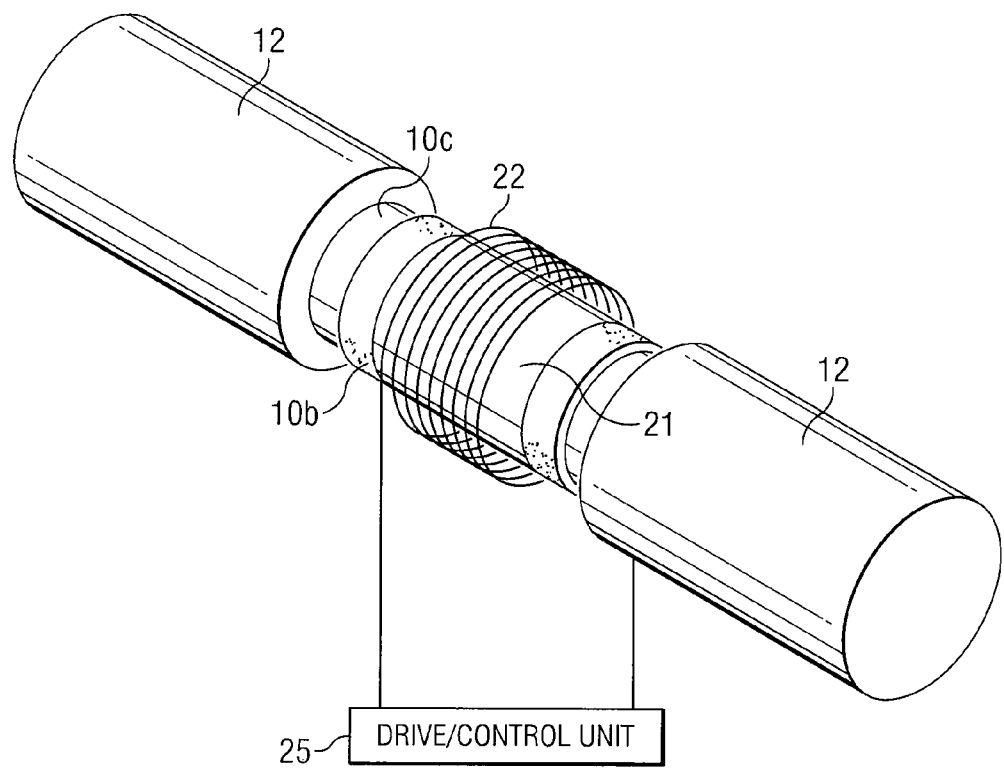
FIG. 2 illustrates a system and method for measuring radial strain of the specimen of FIG. 1.

FIG. 2 illustrates a system and method for measuring the diameter of the powder-filled sleeve 10b. As stated above, the sleeve material is conductive, or alternatively sleeve 10b has a conductive band around at least a portion of its circumference.

In the example of FIG. 2, the specimen 10a is contained in a sleeve 10b, and a conductive band 21 encircles the sleeve 10b. An example of a suitable material for conductive band 21 is copper. In other embodiments, sleeve 10b may itself be made from a conductive material or may contain embedded particles of a conductive material. In all these cases, and in the most general sense, sleeve 10b can be said to have a circumferential band of conductive material.

Sleeve 10b is arranged coaxially relative to an ECT (eddy current test) coil 22. An example of a suitable material for coil 22 is solid copper magnet wire.

For simplicity of illustration, chamber 13 is not shown in FIG. 2, but in practice, specimen 10 and coil 22 are in chamber 13, as indicated by FIG. 1. Electrical connections into chamber 13 from drive/control unit 25 are not shown, but may be implemented with high pressure feed-throughs.

Eddy currents are induced in the conducting material of sleeve 10b, using drive/control circuit 25. Changes in diameter of sleeve 10b affect the coil impedance.

As is known for other applications, eddy current testing is based on the use of a wire coil, energized with alternating current, that induces the flow of eddy currents in a test piece via transformer action. The magnetic field from these currents interacts with the magnetic field from the coil and results in a change in the electrical impedance of the coil. Changes in the electrical characteristics of the test piece (e.g. presence of defects) or electromagnetic coupling to it (e.g. changes in distance from the coil to the test piece) result in changes in the electrical impedance of the coil. These changes are monitored and associated with the parameter to be measured.

In a similar manner, drive/control circuitry 25 may be used to send an electrical drive signal to coil 22, and to receive a response signal from coil 22. A change in impedance is related to the change in diameter of sleeve 1b and hence the radial strain of specimen 10.

Figure 3:
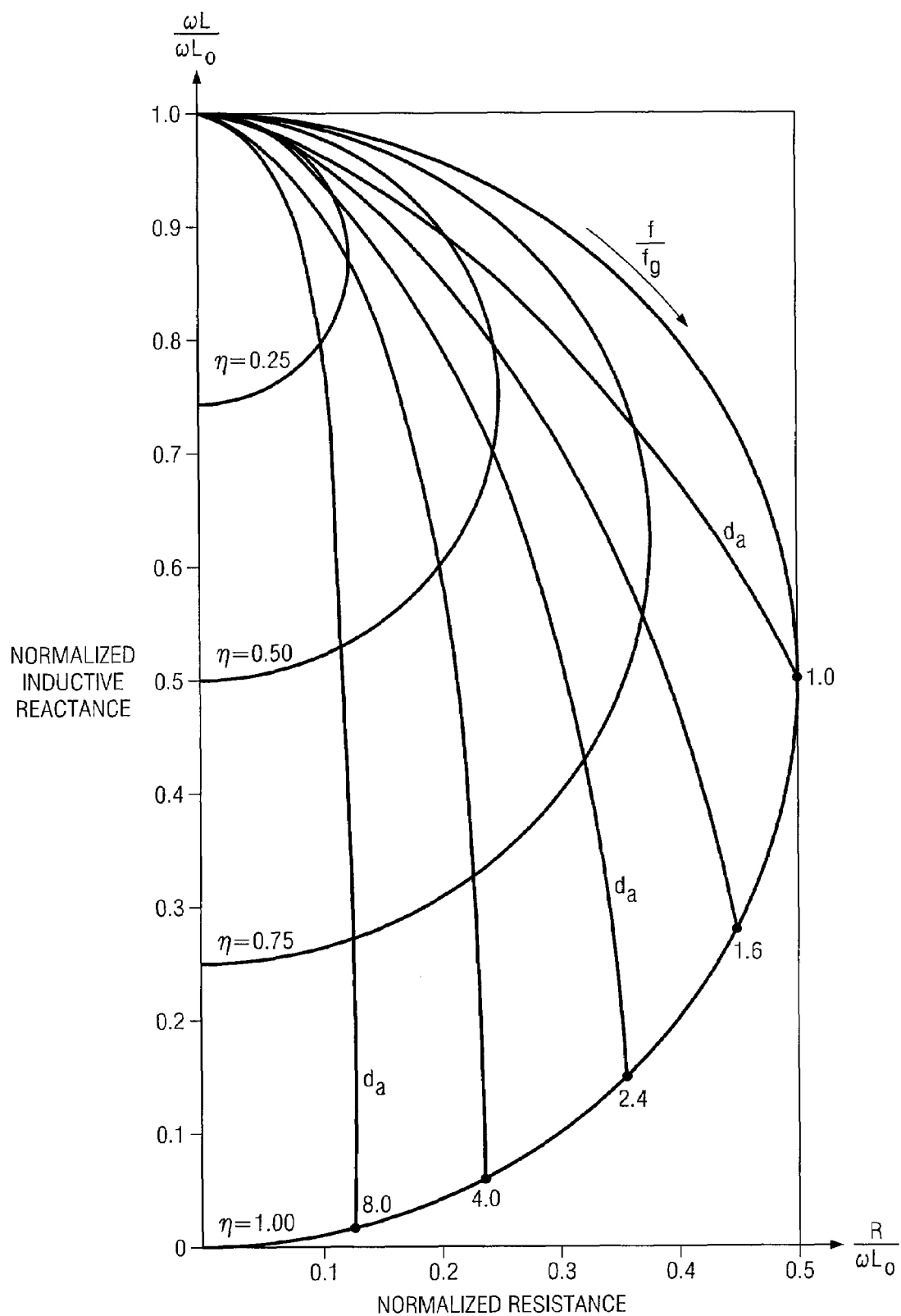
FIG. 3 illustrates how changes in the diameter of a conductive sleeve affect the response of an encircling eddy current coil.

FIG. 3 is an example of an inductive response of copper coil to changes in diameter of a copper sleeve. More specifically, the diagram of FIG. 3 is a complex signal plane for eddy current coil impedance in response to the diameter changes. The value f is test frequency, and $f_g$ is the limit frequency (not important for this discussion). The value η represents the fill factor or diameter of the specimen as a fraction of the coil diameter, and the value da is the specimen diameter. L is the inductance of the coil.

The vertical axis is the reactance of the coil, and the horizontal axis is the resistance. In each case, the values are normalized to the value without a specimen in the coil. As the frequency, f, is increased (relative to the limit frequency $f_g$), the operating point moves around the semicircular curves as designated by the arrow labeled $f/f_g$.

For a given frequency, the coil reactance and resistance change with coil diameter along a line labeled $d_a$, and vary according to the curves labeled η, which represent different fill factors or coil diameters. The specimen diameter can be measured by the variation in coil impedance, according to these curves.

To measure diameter variations with 0.5 μs resolution, coil 22 is excited at a frequency of 15 to 20 MHz. The modulation of this signal is measured as the diameter changes. The method is capable of measuring with a time resolution of 0.5 μs over an interval of 50 μs. The strain rate may be as high as 1000 1/s.

Typically, drive/control unit 25 has a lock-in amplifier. This permits phase-dependent components of the signal to be determined and reconstructed in the complex plane.

Drive/control unit 25 may have appropriate processing and memory for performing an analysis of the electrical response from coil 22. Specifically, unit 25 may have memory for storing the relationships illustrated in FIG. 3, and for relating the response of coil 22 to changes in diameter of the sleeve 10b. Unit 25 may be further programmed to relate the changes in diameter to constitutive properties such as a strain value. Unit 25 may also have timing and control circuitry for controlling the measurement rate. Drive/control unit 25 could be separate from, or integrated with, other control circuitry for controlling the test equipment (i.e., the compression applied by bars 12 and hydraulic fluid in chamber 13).

In sum, the system and method described herein permit radial strain measurements caused by increasing axial load to be made, while the specimen is in hydraulic fluid confinement, imparting radial pressure to the specimen. This method allows quantification of the fundamental response of powder and granular materials to such loading forces.

What is claimed is:

1. A method for measuring radial strain of a sample of a powder, comprising:
   filling a cylindrically shaped pliable sleeve with a sample of the powder;
   wherein the sleeve has a circumferential band of conductive material;
   placing the sleeve within an eddy current coil, such that the sleeve is coaxial with the coil;
   applying at least one compressive force to the sample, such that the diameter of the sleeve changes;
   applying an electrical signal to the coil;
   receiving the electrical eddy current response signal of the coil to changes in the diameter of the sleeve;
   quantatively relating the response signal to the diameter of the sleeve; and
   relating the diameter of the specimen to a constitutive property of the powder.

2. The method of claim 1, wherein the compressive force is an axial force on the sample from each end of the sleeve.

3. The method of claim 1, wherein the axial force is applied to a cap on each end of the sleeve.

4. The method of claim 1, wherein the compressive force is radial loading achieved by placing the sleeve in a hydraulic chamber.

5. The method of claim 1, wherein the circumferential band is the material of the sleeve.

6. The method of claim 1, wherein the circumferential band is a band encircling the sleeve.

7. The method of claim 1, wherein the circumferential band is formed by embedding conductive material into at least a portion of the sleeve.

8. The method of claim 1, wherein the sleeve is made from an elastomeric material.

9. The method of claim 1, wherein the constitutive property is radial strain.

10. A system for measuring radial strain of a specimen of powder contained in a cylindrically shaped pliable sleeve, the sleeve having a circumferential band of conductive material, comprising:

test equipment for applying at least one compressive force to all or part of the sleeve, such that the diameter of the sleeve changes size;

wherein the test equipment has a hydraulic chamber for applying compressive force to the sleeve when the sleeve is installed into the chamber;

an eddy current coil in the chamber, such that the sleeve is coaxial with the coil when installed into the chamber;

a drive/control unit for applying an electrical drive signal to the coil, and for receiving an electrical response signal from the coil.

11. The system of claim 10, wherein the drive/control unit has data processing and storage circuitry for quantatively relating the response signal to the change in the diameter of the sleeve.

12. The system of claim 11, wherein the data processing and storage circuitry stores data that relates changes in diameter of the sleeve to a constitutive property of the material.

13. The system of claim 12, wherein the constitutive property is radial strain.

* * * * *